US010045747B2

(12) United States Patent
Karim et al.

(10) Patent No.: US 10,045,747 B2
(45) Date of Patent: Aug. 14, 2018

(54) SYSTEM AND METHOD FOR A X-RAY DETECTOR

(71) Applicants: Karim S Karim, Waterloo (CA); Ian A. Cunningham, London (CA); Sebastian Lopez Maurino, Toronto (CA)

(72) Inventors: Karim S Karim, Waterloo (CA); Ian A. Cunningham, London (CA); Sebastian Lopez Maurino, Toronto (CA)

( * ) Notice: Subject to any disclaimer, the term of this patent is extended or adjusted under 35 U.S.C. 154(b) by 0 days.

(21) Appl. No.: 15/435,566

(22) Filed: Feb. 17, 2017

(65) Prior Publication Data

US 2017/0238887 A1  Aug. 24, 2017

Related U.S. Application Data

(60) Provisional application No. 62/297,345, filed on Feb. 19, 2016.

(51) Int. Cl.
*A61B 6/00* (2006.01)

(52) U.S. Cl.
CPC ............ *A61B 6/4241* (2013.01); *A61B 6/463* (2013.01); *A61B 6/482* (2013.01); *A61B 6/5217* (2013.01); *A61B 6/5235* (2013.01)

(58) Field of Classification Search
CPC ....... A61B 6/4241; A61B 6/463; A61B 6/482; A61B 6/5217; A61B 6/5235; G01T 1/2018; G01T 1/24; G01T 1/36
See application file for complete search history.

(56) References Cited

U.S. PATENT DOCUMENTS

| 5,548,123 | A  |    | 8/1996  | Perez-Mendez et al. |
|-----------|----|----|---------|---------------------|
| 7,435,965 | B2 |    | 10/2008 | Fuchs et al.        |
| 2010/0092060 | A1 | * | 4/2010 | Bruder ............... A61B 6/032 382/131 |
| 2012/0189100 | A1 | * | 7/2012 | Liu ................... G01T 1/247 378/62 |
| 2012/0223240 | A1 |    | 9/2012 | Ichimura et al.      |
| 2012/0288062 | A1 | * | 11/2012 | Takasaki ............. A61B 6/5205 378/62 |
| 2013/0101082 | A1 | * | 4/2013 | Jordan ................ A61B 6/4035 378/19 |

(Continued)

FOREIGN PATENT DOCUMENTS

WO  WO2015/168147 A1 * 11/2015

OTHER PUBLICATIONS

Canadian Intellectual Property Office as International Searching Authority, International Search Report and Written Opinion on PCT Patent Appln. No. PCT/CA2017/050208, dated May 19, 2017.

*Primary Examiner* — Edward Park
(74) *Attorney, Agent, or Firm* — Gowling WLG (Canada) LLP; Jeffrey W. Wong

(57) ABSTRACT

The disclosure is directed at a method and apparatus for a flat panel X-ray imaging detector. In one embodiment, the apparatus includes three (3) layers including a top layer, an intermediate layer and a bottom layer. The top layer generates a top layer image; the intermediate layer generates an intermediate layer image; and the bottom layer generates a bottom layer image. The intermediate layer also operates simultaneously as an intermediate X-ray energy filter.

6 Claims, 11 Drawing Sheets

Diagram depicting the two possible X-ray paths of main interest.

(56) References Cited

U.S. PATENT DOCUMENTS

| | | | |
|---|---|---|---|
| 2013/0279785 A1* | 10/2013 | Proksa | G06T 11/006 |
| | | | 382/131 |
| 2014/0119668 A1* | 5/2014 | Kwon | G06T 11/005 |
| | | | 382/232 |
| 2014/0321616 A1 | 10/2014 | Gibson | |
| 2015/0103976 A1* | 4/2015 | Kang | A61B 6/542 |
| | | | 378/62 |
| 2016/0038111 A1* | 2/2016 | Maidment | A61K 49/0423 |
| | | | 600/431 |
| 2016/0296194 A1* | 10/2016 | Kang | A61B 6/481 |
| 2016/0372136 A1* | 12/2016 | Song | G06K 9/00718 |
| 2017/0109904 A1* | 4/2017 | Huang | G06T 11/008 |
| 2017/0172528 A1* | 6/2017 | Wiedmann | A61B 6/482 |
| 2017/0238887 A1* | 8/2017 | Karim | A61B 6/4241 |

* cited by examiner

Figure 3: Diagram depicting the two possible X-ray paths of main interest.

SYSTEM AND METHOD FOR A X-RAY DETECTOR

CROSS-REFERENCE TO OTHER APPLICATIONS

This application claims the benefit of U.S. Patent Provisional Application No. 62/297,345, filed Feb. 19, 2016, which is incorporated herein by reference.

FIELD OF THE DISCLOSURE

The disclosure is generally directed at X-ray imaging and, more specifically, to a system and method for a flat panel X-ray imager.

BACKGROUND OF THE DISCLOSURE

Several radiography diagnostic and screening techniques depend on the visualization of small objects having a high attenuation coefficient embedded in a cluttered soft-tissue environment. These include, but are not limited, coronary angiography (where a contrast agent is added to blood vessels in the heart to assess cardiovascular diseases) and calcification detection in chest radiography (where the benignity of pulmonary nodules is characterized by its calcium content). Enhancing the detectability of these objects is, therefore, very desirable.

A technique that has long been proposed to achieve this is that of dual-energy (DE) subtraction imaging, which exploits the different energy-dependence of the X-ray attenuation coefficient of different tissue types to remove the soft-tissue component from the radiographic image and hence enhance visualization of the objects of interest.

DE systems work by obtaining one low-energy and one high-energy image, and performing a weighted subtraction to combine them into a final image (for display) in which the cluttered soft-tissue structure has been removed.

An alternative DE imaging method is the single-shot approach, in which both images are obtained simultaneously. This is accomplished by stacking two sensor layers vertically to form a two-layer detector in what is known as a sandwich configuration. The spectral separation results from a combination of the intrinsic higher probability of high-energy photons to go through the top layer unabsorbed and the presence of a metal beam-hardening mid-filter in between the two layers. Single-shot techniques are thus much more tolerant to both patient and cardiac motion than kVp switching, and are compatible with most current X-ray sources. However, the presence of the hardening mid-filter means that a portion of the X-rays are wasted in it, resulting in patient dose inefficiency.

Therefore, there is provided a novel X-ray imager that overcomes disadvantages of current systems.

SUMMARY OF THE DISCLOSURE

The disclosure is directed at a detector having at least three layers to be used for X-ray imaging including a top layer, an intermediate layer and a bottom layer. In one embodiment, the disclosure can be used as a single-shot dual energy (DE) imager. In the current embodiment, each layer of the imager, or detector, includes a sensor coupled to a scintillator layer or semiconductor material layer of specific thickness. The top and bottom layers generate low and high energy images respectively while the intermediate layer acts as a filter to harden the beam before it reaches the bottom layer and can also, simultaneously, generate an image (from received energies).

As such, the system of the disclosure can then operate in many distinct modes. One example is in full spectrum X-ray mode in which the signal from all three layers is simply added or combined through a weighted average to form a single image. In this mode, no dose delivered to the patient is wasted and the image obtained will display information from the entire X-ray spectrum used akin to a regular radiographic detector. A second example mode is that as a DE imager, in which only the signals from the top and bottom layers are used or manipulated to acquire an image without any clutter such as from the soft-tissue of the patient. All of the detector's modes (including these two examples) are not mutually exclusive whereby the imager can operate in all modes simultaneously since all the necessary data is captured in a single X-ray exposure.

In one aspect of the disclosure, there is provided apparatus for an X-ray detector including a top layer for detecting X-rays and generating a top layer image; an intermediate layer for detecting X-rays and generating an intermediate layer image; and a bottom layer for detecting X-rays and generating a bottom layer image; wherein the intermediate layer also operates simultaneously as an intermediate X-ray energy filter.

In another aspect, the top, intermediate and bottom layers include a direction conversion X-ray detector. Alternatively, the top, intermediate and bottom layers include an indirection conversion X-ray detector. In a further aspect, the system may include a top layer scintillator layer integrated within the top layer; an intermediate scintillator layer integrated within the intermediate layer; and a bottom layer scintillator layer integrated within the bottom layer.

In a further aspect, the intermediate layer is sensitive to an intermediate energy spectrum. In another aspect, the top layer is sensitive to a lower energy spectrum and the bottom layer is sensitive to a high energy spectrum.

In a second aspect of the disclosure, there is provided a method of X-ray imaging including obtaining a set of at least three images including a high energy image, an intermediate energy image and a low energy image; combining the at least three images to generate a full spectrum X-ray image; and manipulating at least two of the at least three images to generate at least one enhanced X-ray image.

In yet another aspect, manipulating the at least two of the at least three images includes selecting the high energy image and the low energy image; and combining the high energy image and the low energy image to generate a new set of dual-energy images.

In a further aspect, manipulating the at least two of the at least three images includes selecting the high energy image, the intermediate energy image and the low energy image; obtaining high energy spatial image data, intermediate energy spatial image data and low energy spatial image data; identifying scattered radiation using the high energy spatial image data, intermediate energy spatial image data and low energy spatial image data; and manipulating the high energy image, the intermediate energy image and the low energy image to generate a set of scatter noise reduced images.

In yet another aspect, manipulating the at least two of the at least three images includes selecting the high energy image, the intermediate energy image and the low energy image; mapping the high energy image, the intermediate energy image and the low energy image into color channels; and generating a color X-ray image based on the mapping.

In another aspect, manipulating the at least two of the at least three images includes selecting the high energy image, the intermediate energy image and the low energy image; manipulating the high energy image and the intermediate energy image to generate an intermediate-high energy image; manipulating the low energy image and the intermediate energy image to generate an intermediate-low energy image; and manipulating the high energy image, the intermediate-high energy image, the intermediate energy image, the intermediate-low energy image and the low energy image to generate a set of spectrally enhanced dual energy images.

In an aspect, manipulating the at least two of the at least three images includes selecting the high energy image, the intermediate energy image and the low energy image; manipulating the intermediate energy image data to enhance the signal-to-noise ratio of the low energy image and the high energy image; and manipulating the high energy image, the intermediate energy image and the low energy image to generate a set of higher signal-to-noise ratio dual energy images.

DESCRIPTION OF THE DRAWINGS

Embodiments of the present disclosure will now be described, by way of example only, with reference to the attached Figures.

FIG. 1b is a schematic diagram of a three-layer X-ray imager for use in the system of FIG. 1a;

DETAILED DESCRIPTION

The disclosure is directed at a method and apparatus for a flat panel X-ray imaging detector. In one embodiment, the apparatus includes at least three (3) layers including a top layer, an intermediate layer and a bottom layer. In another embodiment, the intermediate layer simultaneously operates to receive intermediate level energy from X-ray beams and to act as a intermediate X-ray energy filter. The intermediate frequencies or energies may then be transmitted to a processor to enable further applications of the X-ray imaging detector of the disclosure.

Figure 1A:
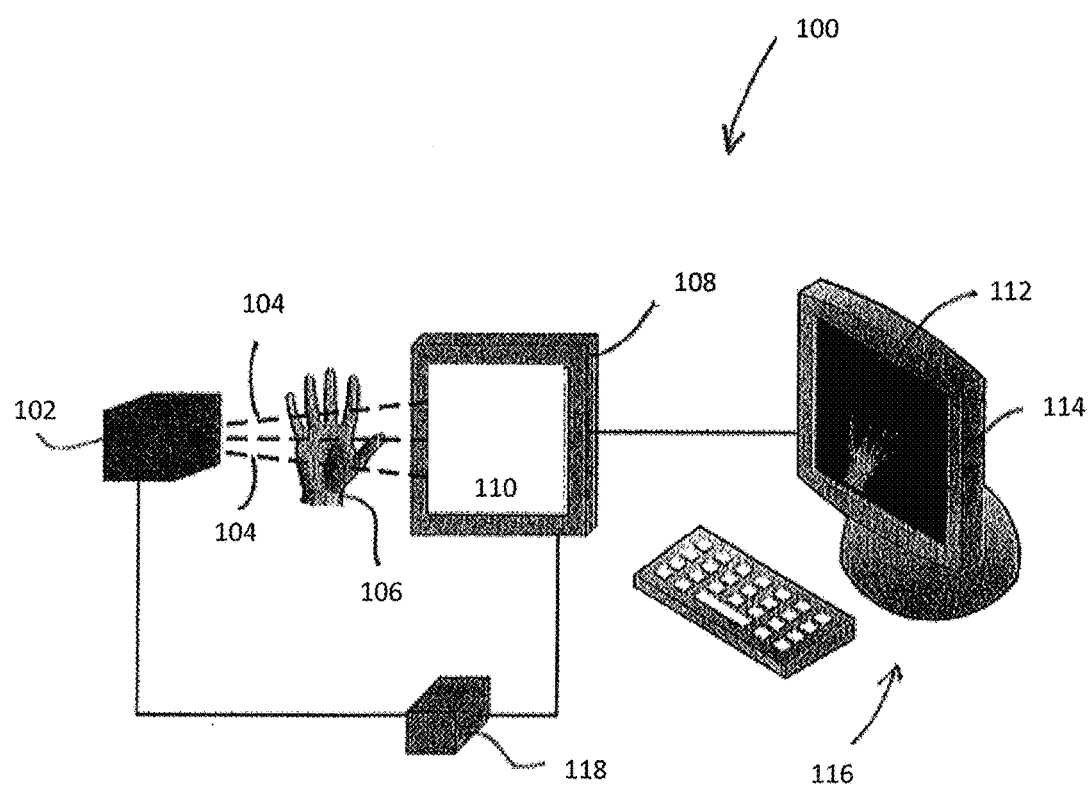
FIG. 1a is a schematic diagram of a system for X-ray imaging.

FIG. 1a illustrates a schematic diagram of an imaging environment, or system for X-ray imaging. The system 100 includes an X-ray radiation source 102 that generates X-ray radiation, in the form of a set of X-ray beams 104, that is transmitted towards an object of interest 106 (such as a patient's hand), for imaging by an X-ray detector system 108. In the present disclosure, the X-ray detector system 108 preferably includes an X-ray image detector 110 to detect the transmitted portion of the X-ray beams 104 in order to produce an image 112 of the object 106. In general, the object 106 to be imaged is positioned between the X-ray radiation source 102 and the X-ray detector system 108 such that the X-rays pass through the object 106 and interact with the X-ray detector system 108. The created image 112 can then be displayed for viewing on a display 114, or monitor, of a computer system 116. Alternatively, the image 112 may be stored in memory, or a database (not shown) for later retrieval.

For some X-ray detector systems 108, synchronization hardware 118 may be necessary to obtain the correct timing between the X-ray source 102 and the X-ray detector system 108 that is sampling the impinging transmitted portion of X-ray beams 104.

Figure 1B:
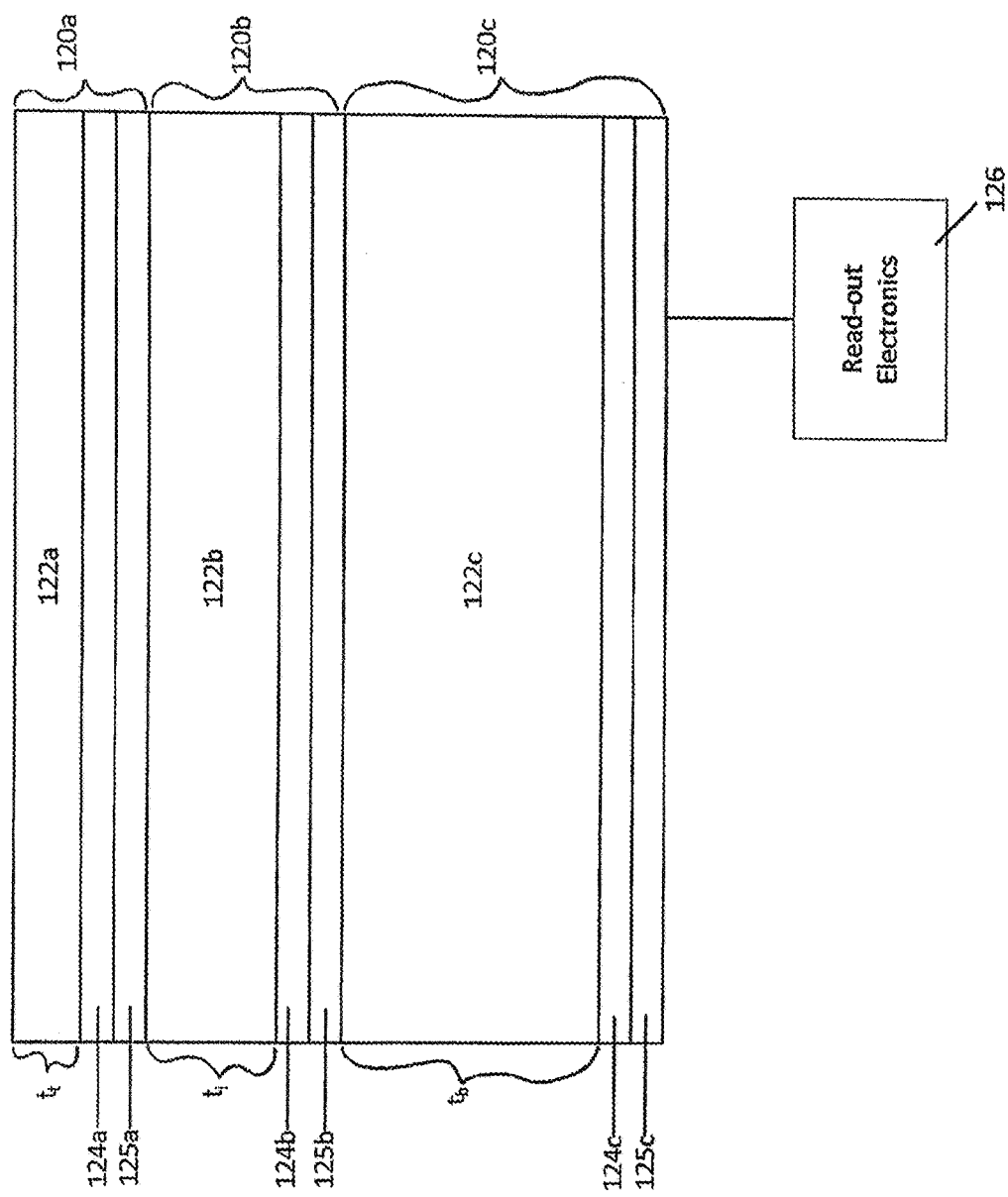
Figure 2:
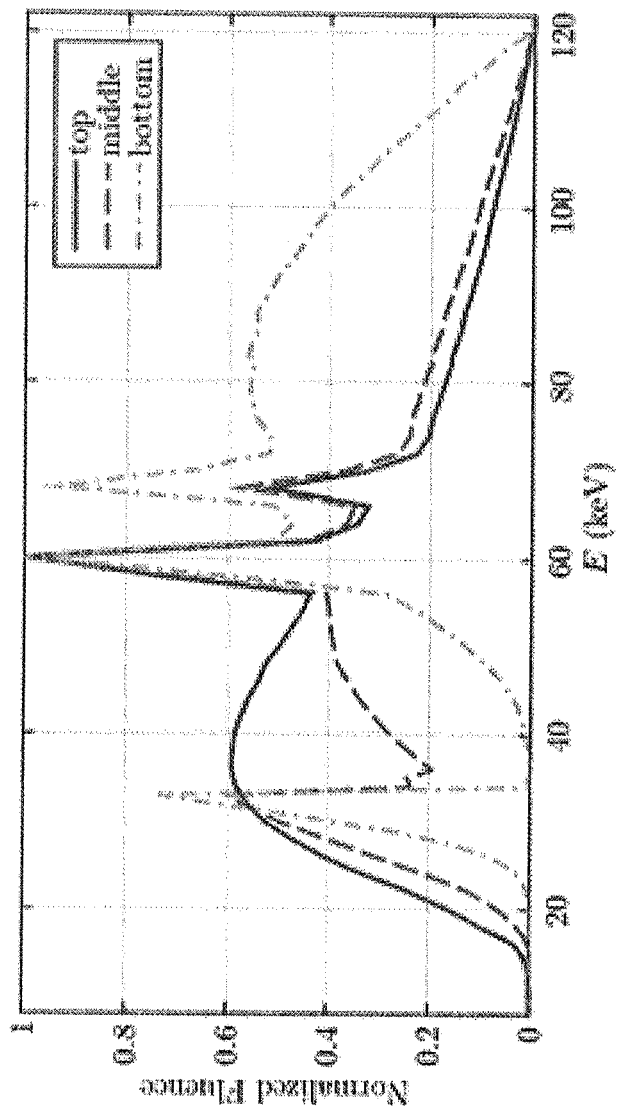
FIG. 2 is a graph showing an example of the different incident X-ray spectra on each layer of the detector.

Turning to FIG. 1b, a schematic diagram of an X-ray image detector in accordance with an embodiment of the disclosure is shown. In the preferred embodiment, the X-ray imaging detector 110 includes a set of three layers 120 seen as a top layer 120a, an intermediate, or middle layer 120b and a bottom layer 120c. These layers 120 are stacked in such a way that, when oriented in the X-ray imaging environment, the X-ray beam 104 will go through the object 106 and sequentially reach each layer. First, the X-ray beam 104 will reach the top layer 120a; next, the remaining portion of the X-ray beam 104 will reach the intermediate layer 120b; and next, what remains of the X-ray beam 104 will reach the bottom layer 120c.

Each layer 120 of the detector 110 includes an X-ray sensitive material layer 122. For an X-ray imaging detector 110 operating in an indirect mode, this X-ray sensitive material layer may be a scintillator or scintillator layer. For an X-ray imaging detector 110 operating in a direct mode, this X-ray sensitive material layer may be manufactured from a semiconductor material. Each layer 120 may be distinguishable from the other layers by the physical properties of this X-ray sensitive material, such as Gadolinium oxysulfide or cesium iodide. Alternately, the layers may be distinguished by the thickness of this material, seen as $t_t$, $t_i$ and $t_b$, in FIG. 1b, where the subscript t represents top, the subscript i represents intermediate and the subscript b represents bottom. Each layer 120 also includes a sensor layer 124 coupled to the X-ray sensitive material layer 122. In one embodiment, the sensor layer is manufactured from using a large area thin film silicon semiconductor such as, but not limited to, amorphous silicon, polysilicon, organic semiconductor, Indium Gallium Zinc Oxide on top of a substrate layer 125. The sensor layer 124 preferably includes a region that can be considered to be subdivided into pixels whereby each pixel contain a thin-film transistor (TFT) and a sensor.

In an embodiment where the layer 120 acts as an indirect converter, photodiodes associated with each TFT generate a signal related to the light generated by the X-ray sensitive scintillator sitting atop the sensor layer. In an embodiment where the layer 120 acts as a direct X-ray converter, electrodes associated with each TFT generate a signal related to the current in the X-ray sensitive semiconductor material. In direct X-ray converters, there is no need for a scintillator and photodiode since the X-ray semiconductor direct converts X-rays into electronic charge. In either embodiment, the TFTs will pick up these signals, which are then transmitted to other read-out electronics 126 that allow for the generation of an image, or images, 112 based on these signals. Using the necessary circuitry and computing device, each layer can capture, or acquire an individual image which may then be processed before being displayed or saved. In place of a TFT based X-ray detector, a large area silicon CMOS based X-ray detector may also be employed as would be understood by one skilled in the art.

In operation, the X-ray beam 104 is directed towards the X-ray imaging detector 110 such that it passes through the object 106 before it reaches the detector 110. An X-ray beam typically contains X-ray photons with energies across the diagnostic X-ray energy range. The exact details of this energy spectrum will depend on the characteristics of the X-ray source 102. These characteristics include, but not be limited to, the source operating voltage, the anode material, the filtering materials or the filter thickness.

Upon reaching the detector 110, the X-ray beam 104 will reach the top layer 120a of the detector 110. Due to the energy-dependent nature of X-rays and the matter interaction of X-rays of lower energy having a higher chance of interacting with matter, this layer 120a will probabilistically absorb more of the lower end of the incident X-ray, or energy, spectrum of the X-ray beam 104 and generate a top layer, or low energy, image. This implies that the image that is generated by the top layer 120a will be more closely associated with the lower end of the X-ray energy spectrum. The remainder of the X-ray beam 104 proceeds to the intermediate layer 120b. Here, the intermediate layer will preferentially absorb the lower energy end of the spectrum of the remaining photons, leaving an X-ray beam 104 with higher mean energy to proceed to the bottom layer 120c. At the same time, an intermediate layer, or intermediate energy, image is created, or generated, in the intermediate layer that corresponds to those photons absorbed in it. Finally, this X-ray beam of higher mean energy reaches the bottom layer 120c, where a portion of it will be absorbed and a bottom layer, or high energy, image can be generated using most, if not all, of the remaining photons of higher mean energy than the previously mentioned. Through this process, an advantage of the current disclosure is achieved in that three independent images, each of which is formed with different spectral information of increasing mean energy, can be obtained during a single X-ray exposure.

During an exposure, the role of the intermediate layer 120b of this detector 110 is twofold. The intermediate layer 120b simultaneously (1) acts as a spectral filter to allow for a larger difference of the mean energy of the incoming spectra between the top and bottom layers, as well as (2) acts as a sensitive layer itself to produce a signal that can be used to either improve the images obtained by the other layers or create new types of images. This twofold operation of the intermediate layer is an advantage of the disclosure over existing detector design.

The presence of the intermediate layer 120b that simultaneously acts as both a filter and an X-ray sensor allows the detector of the disclosure to function in several different modes (as outlined in more detail below). Each mode is distinct in the way in which the signal from the intermediate layer 120b is used (or not used) or combined (or not combined) with the images from the top and bottom layers to generate one or more final images.

In other words, the imaging detector 110 of the disclosure is able, in a single X-ray exposure, to simultaneously obtain three separate images that each carry different spectral information, and then process, manipulate and/or combine them (or a subset of them) to generate new, enhanced images. It is these final generated images (or a combination of the images) that are displayed to the user or physician. These images can also be saved for later retrieval.

An advantage of the current disclosure is that the three images generated at each layer each carrying different spectral information are all obtained during the same X-ray exposure. That is, it is only necessary to go through the operation process detailed above once to obtain all three images, resulting in a savings of X-ray radiation dose to the patient and a reduction in motion artifacts. Moreover, once the three different images are obtained, they can be used in any number of combinations without needing to be obtained again. Therefore, multiple different types of enhanced images may be obtained with only a single exposure of a patient to X-ray radiation. As such, a further advantage is that there is a lower dose exposure for a patient with respect to obtaining multiple types of images.

Each mode in which the X-ray imager operates can be seen as being distinct in the way in which one or more resulting images are generated from some or all of the images obtained by each layer of the detector.

An example of one of the possible operational modes of this detector is as a dual energy detector, in which the signals from the top and bottom layers are used as the low and high energy images respectively. These two images can be combined by, for example, logarithmic subtraction to generate two enhanced imaged that allow for easier detection of certain material or tissue types. In this example, the intermediate layer is acting solely as a filter that allows for a higher spectral separation between the top and bottom layers. This higher spectral separation is known to result in better enhanced DE images and better DE capabilities in general.

However, the capabilities of the detector are improved by the presence of the X-ray-sensitive intermediate layer, even in the example mentioned above of a DE detector.

In this example, the fact that this intermediate layer simultaneously acts as both a filter and a sensitive layer improves the detector's capabilities. Moreover, by independently tuning the thickness of all three conversion layers (i.e. scintillators in the case of indirect detection and the semiconductor layer in the case of direct detection), it is possible to obtain the optimal spectral separation needed to create the improved possible enhanced DE images.

Firstly, the signal of the intermediate layer can be used to improve the DE images generated. This can be done by using the information provided by the intermediate layer image in a number of ways. These include, but are not limited to, for example, enhancing the final DE images obtained by reducing the noise in the top or bottom layer images through the use of statistical algorithms that take into account information from the intermediate layer, or, as another example, identifying scatter sources between the top and bottom layers which can allow for a scatter rejection algorithm to reduce scatter noise in the bottom layer.

Secondly, the image generated in the intermediate layer can be used in combination with some or none of those obtained in the other layers to also generate other image types as described by other modes of image combination. This can be done without requiring another X-ray exposure. In other words, even while acting as a DE imager, this disclosure is still capable of simultaneously operating in any other mode described here or developed later on.

As another example of how an operation mode can use the obtained images, if the images from all three layers are combined in simple additive or averaging forms, a full spectrum X-ray image can be generated. This full spectrum X-ray image will contain information across most of (if not all of) the X-ray spectrum emitted by the X-ray source. In other words, it is similar to that of an X-ray detector with a thicker sensitive layer, but advantageously avoids some of the signal-spread issues that a detector with a thicker sensitive layer would likely have. Furthermore, by using the known spatial positions of each layer, inter-layer scatter sources may be identified and the noise they cause in the images can be reduced by employing a scatter correction algorithm.

Another example of image combination is that of colour X-ray images. This is made possible by selecting the image generated at the top layer, the image generated at the intermediate layer and the image generated at the bottom layer, and mapping them to the red, green and blue channels of a colour image. This will result in a clear way of visualizing X-ray spectral information in the form of a colour image and can aid in certain tissue or material type detection.

In another example of the image combination modes, two other possible set of DE images can be generated simultaneously, as well as the previously-mentioned one. That is, as well as combining the signals from the top and bottom layer, it is also possible to generate a set of enhanced DE images by combining the images from the top and intermediate layers, as well as another set by combining the images from the intermediate and bottom layers. This is because the mean energy of absorbed X-ray spectra increases as the X-ray beam passes through each detector layer. Therefore, selecting these other two pairs of images will provide two additional spectrally-distinct images which can be used together with the original three images for generating a new set of enhanced DE images by methods including a weighted subtraction. Each different set of enhanced DE images will highlight different material or tissue types, and hence they may aid material or tissue type detectability or in clutter reduction.

Lastly, the SNR in the bottom layer is often low because a large part of the X-ray signal is deposited in the top layers. A method of combining the images from the intermediate and bottom layer using appropriate weighting functions and filters can also yield an improved SNR in the bottom layer.

Figure 8A:
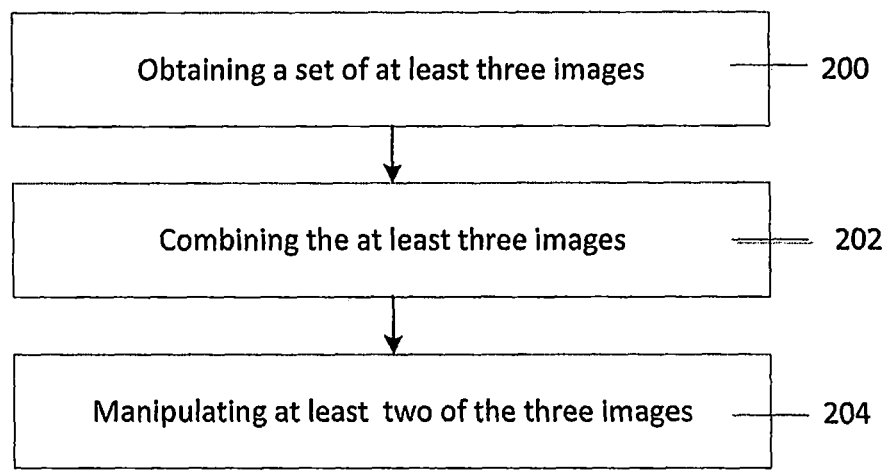
FIG. 8a is a flowchart outlining a method of generating images using an X-ray imaging detector of the disclosure.

Turning to FIG. 8a, a flowchart outlining a method of X-ray imaging is shown. Initially a set of at least three images are obtained, preferably from a single X-ray exposure (200). In a preferred embodiment, these images may be seen as a high energy image, an intermediate energy image and a low energy image. As will be understood, these images are generated based by the top, intermediate and bottom layers of the imaging detector. The images may then be combined (202) to generate, or form a full spectrum X-ray image. At least two of the images may also be manipulated (204) to provide other images (such as previously disclosed). More specifically, the at least two images can be manipulated to generate a new X-ray image.

Figure 8B:
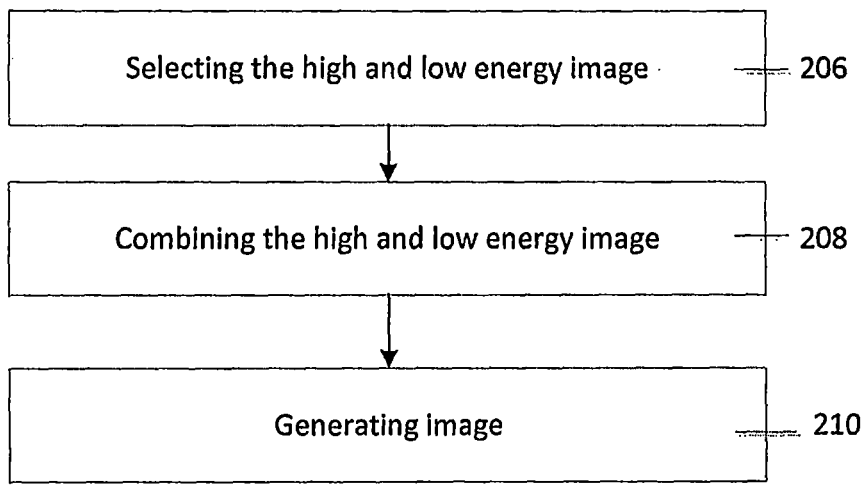
FIG. 8b is a flowchart outlining another embodiment of generating images.

Turning to FIG. 8b, a flowchart outlining a first embodiment of manipulating the at least two images (204) is shown. In the current embodiment, the high and low energy images are selected (206). The high and low energy images are then combined (208) and an image, such as a set of dual-energy images are then generated (210). In one embodiment, the combination (208) is achieved by performing a weighted subtraction of the higher energy image and the low energy image.

Figure 8C:
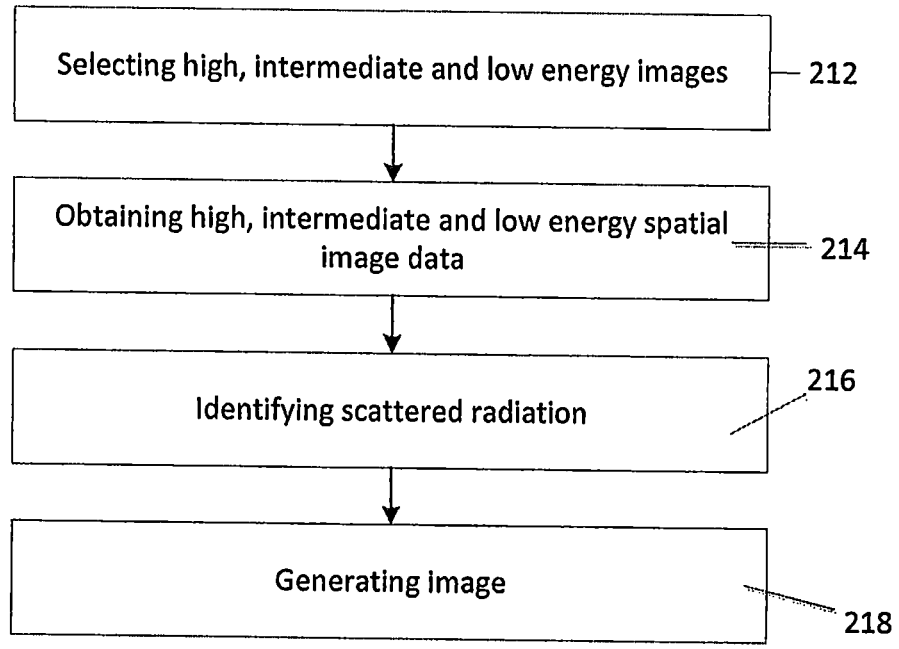
FIG. 8c is a flowchart outlining a further embodiment of generating images.

Turning to FIG. 8c, a flowchart outlining another embodiment of manipulating the at least two images (204) is shown. In the current embodiment, the high, intermediate and low energy images are selected (212). High, intermediate and low energy spatial data is then obtained (214) from the images or via known techniques. Scattered radiation can then be identified (216) using the high, intermediate and low energy spatial data and a set of scatter noise reduced images generated (218). In another embodiment, the set of scatter noise reduced images can be performed by using a scatter noise correction algorithm.

Figure 8D:
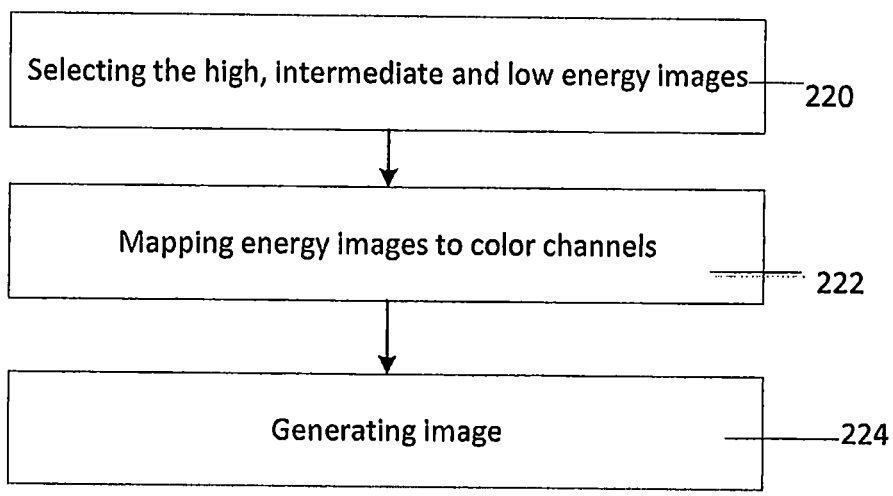
FIG. 8d is a flowchart outlining yet another embodiment of generating images.

Turning to FIG. 8d, a flowchart outlining another embodiment of manipulating the at least two images (204) is shown. In the current embodiment, the high, intermediate and low energy images are selected (220). The images are then mapped to color channels (222) and a color X-ray image can then be generated (224).

Figure 8E:
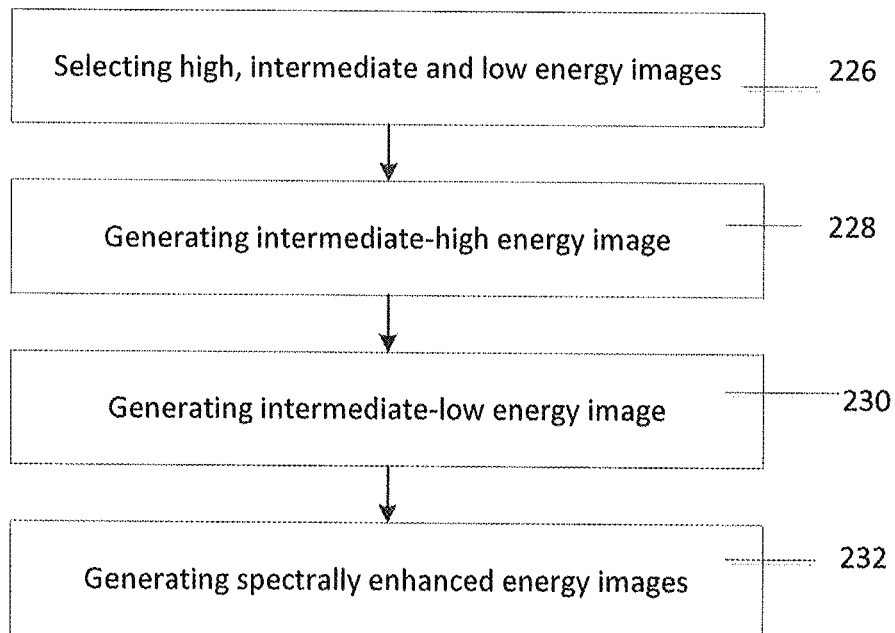
FIG. 8e is a flowchart outlining an embodiment of generating images.

Turning to FIG. 8e, a flowchart outlining another embodiment of manipulating the at least two images (204) is shown. In the current embodiment, the high, intermediate and low energy images are obtained, or selected (226). An intermediate-high energy image is then generated by combining or manipulating the intermediate and high energy images (228). An intermediate-low energy image is then generated by combining or manipulating the intermediate and low energy images (230). A spectrally enhanced image can then be generated (232) based on the high energy image, the intermediate-high energy image, the intermediate energy image, the intermediate-low energy image and the low energy image such as by manipulating the images. In one embodiment, the spectrally enhanced image can be generated performing a weighted subtraction on at least two of the high energy image, the intermediate-high energy image, the intermediate energy image, the intermediate-low energy image and the low energy image.

Figure 8F:
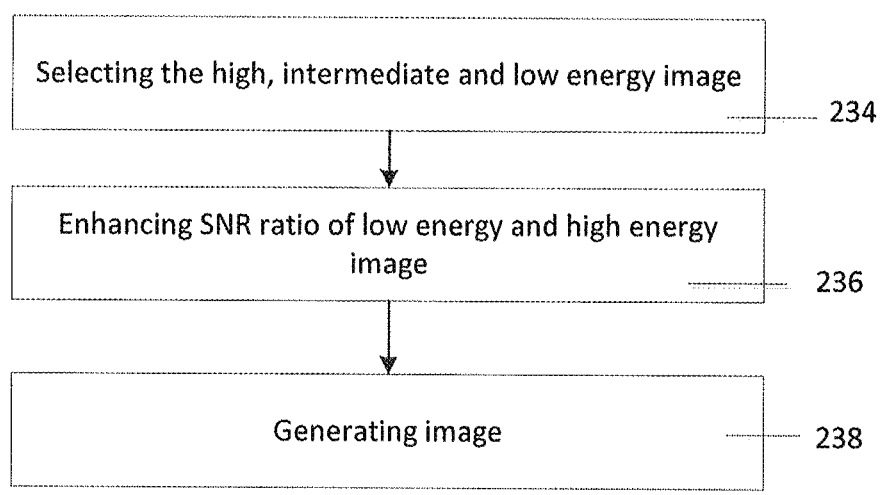
FIG. 8f is a flowchart outlining another embodiment of generating images.

Turning to FIG. 8f, a flowchart outlining another embodiment of manipulating the at least two images (204) is shown. In the current embodiment, the high, intermediate and low energy images are obtained, or selected (234). The signal-to-noise ratio of the low energy and high energy images can then be enhanced by the intermediate energy image (236) and a set of high signal-to-noise ratio images can then be generated (238) such as by performing a weighted subtraction of the enhanced high and low energy images.

In another embodiment, the high, intermediate and low energy images are obtained, or selected and then an addition or weighed average of the high, intermediate and low energy images is performed to generate a fully spectrum X-ray image.

The functionality of this disclosure is not limited to these operational modes described above, but rather these are simply examples of the possible enhanced imagery this detector can be used to create due to its capability of creating three spectrally distinct images during a single X-ray exposure.

An outline of how to design and optimize an embodiment of this disclosure for the purposes of being used partially as a DE imager is presented below. This outline is intended to illustrate one of the many capabilities of the presented disclosure and the type of design process that may go into a particular embodiment. It should be understood by one skilled in the art that the novel combinations and manipulations of spectral image data with the triple layer detector of the disclosure are also possible with a four layer or more detector embodiment.

In the following description, one embodiment of a triple layer X-ray detector in accordance with the disclosure is shown. In the description, the X-ray detector is preferably directed at one for DE imaging with an intermediate layer operating simultaneously as a filter and a detector for intermediate frequencies.

In this example embodiment, a triple layer detector where all sensitive layers act as indirect-detection sensors is disclosed. That is, three layers made up of a cesium iodide scintillator coupled to a FPD stacked such that they form a three-layer detector as described in this disclosure. Cesium iodide was selected as the scintillator material for this example due to its maturity, availability and ability to be grown structurally. This material is also attractive due to its common and established integration with FPD technology. The packing efficiency of the CsI:Tl columnar scintillator was taken to be 75%. While Cesium Iodide was used, other similar materials such as Gadolinium Oxysulfide (GOS) or other scintillators are contemplated. Alternately, different thickness of direct X-ray conversion semiconductor for the three-layer detector could also be employed.

Two example target application are selected: iodinated vessels detection in coronary angiography and pulmonary calcifications detection in chest radiography. Both are cases of a smaller object of relatively high X-ray attenuation coefficient embedded in soft tissue. Therefore, both are cases where DE imaging can be beneficial.

Figure 3:
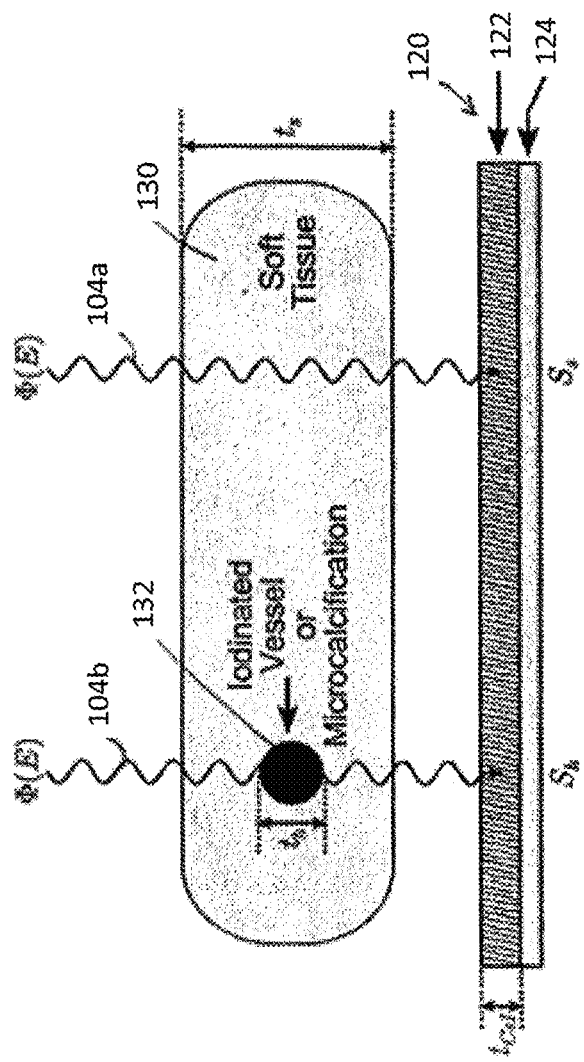
FIG. 3 is a schematic diagram of two selected X-ray paths in example applications.

FIG. 3 is a schematic diagram of a single exposure of an X-ray beam 104, or spectrum (seen as $\phi(E)$) that is measured in (photon/(cm² keV)) through an object 106 that is directed to an X-ray image detector 110. For discussion purposes, in the current example, the X-ray imager 110 is a single layer or single scintillator-based FPD. This was used to determine signal and noise characteristics for single layer imagers. Schematically, the apparatus of the disclosure (such as shown in FIG. 1b) may be seen as a set of three-single layer scintillator based FPDs.

As shown in FIG. 3, two X-ray paths stand out: 1) a first X-ray beam 104a that will only go through soft tissue 130 (of thickness $t_s$ (in cm)) before reaching the detector or layer 120, and 2) a second X-ray beam 104b that will go through an iodinated vessel 132 or calcification (of thickness $t_h$ (in cm)) as well as its surrounding soft tissue 130 before reaching the detector, or layer 120. For clarity and explanation, the first X-ray beam results in a detector signal $S_s$ while the second X-ray beam results in a detector signal $S_h$. As can be seen the layer 120 includes a scintillator layer 122 and a substrate layer 124.

The expected mean signals $\bar{S}_s$ and $\bar{S}_h$ for a pixel of size A (mm²) located entirely in one of the X-ray beam paths may be calculated using the equations:

$$\bar{S}_s = A\int_0^\infty \Phi(E) e^{-\mu_s(E)t_s} \eta(E) \bar{Q}_{CsI}(E) dE \quad (1)$$

$$\bar{S}_h = A\int_0^\infty \Phi(E) e^{-\mu_s(E)(t_s-t_h)-\mu_h(E)t_h} \eta(E) \bar{Q}_{CsI}(E) dE \quad (2)$$

where $\mu_s(E)$ and $\mu h(E)$ are the X-ray attenuation coefficients (cm⁻¹) of soft tissue and the iodinated vessel or calcification, respectively at an X-ray photon energy E (keV), $\eta(E)$ is the X-ray absorption ratio of the scintillator layer (i.e. its quantum efficiency), and $\bar{Q}_{CsI}(E)$ is the mean of the scintillator gain function. For simplicity, it is assumed that the attenuation coefficients are constant throughout for the soft tissue and the iodinated vessel.

The quantum efficiency of the scintillator layer is given by:

$$\eta(E) = 1 - e^{\mu_{CsI}(E)t_{CsI}} \quad (3)$$

where $\mu_{CsI}(E)$ is the attenuation coefficient of the scintillator layer (also considered constant) and $t_{CsI}$ is the thickness of the scintillator. It is, typically, the portion of incoming X-ray photons that will be absorbed by the scintillator layer.

The scintillator gain function, $\tilde{Q}_{CsI}(E)$ is a random variable that corresponds to the number of optical photons generated in the scintillator due to an incoming X-ray of energy (E). This means that the generated signals $\tilde{S}_s$ and $\tilde{S}_h$ are compound random variables, given that the number of photons that will reach the pixel, N, will follow a Poisson distribution. However, since the number of scintillator photons generated for a typical X-ray is small (e.g. a cesium iodine scintillator can generate ~1500 optical photons for a 25 keV photon) when compared to N, its contribution to the signal variance can be neglected and only its mean value needs to be considered. This value, in turn, can be expressed as:

$$\bar{Q}_{CsI}(E) = \gamma(E) E_{abs}(E) \quad (4)$$

where $\gamma(E)$ (photons/keV) is the mean number of photons generated and collected in the scintillator layer by an absorbed photon of energy E, and $E_{abs}(E)$ is the energy absorbed in the scintillator due to an X-ray photon of energy (E) interacting in it. For a common inorganic scintillator, this gain is nearly proportional to the deposited radiation, removing the energy dependence of the number of photons generated ($\gamma(E)=\gamma$) and reducing Equation (4) to $\bar{Q}_{CsI}(E) = \gamma E_{abs}(E)$.

From these calculations, an expression for the expected variance in each one of the signals that result from the contributions of these two random variables can be generated. This expressions are:

$$\sigma'^2_s = A\int_0^\infty \Phi(E) e^{-\mu_s(E)t_s} \eta(E) \bar{Q}_{CsI}^2(E) dE \quad (5)$$

$$\sigma'^2_s = A\int_0^\infty \Phi(E) e^{-\mu_s(E)(t_s-t_h)-\mu_h(E)t_h} \eta(E) \bar{Q}_{CsI}^2(E) dE \quad (6)$$

Further experimentation to determine K-edge considerations were also performed. When the energy of the X-ray photons incident on the scintillator exceeds one of its K-edge energies, some of this energy will be lost in escaping characteristic X-ray emission. This is accounted for in $E_{abs}(E)$ as a part of the scintillator gain $Q_{CsI}(E)$. $E_{abs}$ has previously been calculated to be linearly dependent on E both below and above the K-edge energies, while showing considerable dips at those energies.

Another factor to consider is the blur which may result from the scintillator layer. The needle-like structure of CsI:Tl scintillators has been shown to guide light towards the top and bottom surfaces of a phosphor screen of the imager and reduce lateral spread, thereby increasing spatial resolution. However, theoretical and simulation analyses of these structured scintillators have shown that a portion of the light quanta generated in the scintillator will still travel laterally and contribute to optical blur. This spatial spreading of the signal affects the resolution of the imager and reduces the spatial noise variance.

An analytical model was used to approximate this noise reduction by considering how the signal of an infinitely thin monoenergetic X-ray pencil beam of energy E spreads in a CsI:Tl structured scintillator of thickness $t_{CsI}$ before reaching the detector plane. This is known as the Point Response Function (PRF) of the system and represents its deterministic phosphor blur. Its value at any point on the detector (x, y) is a function of these parameters, and so PRF=PRF(x, y, E, $t_{CsI}$).

As will be understood, this scintillator blur will affect the detector's signal variance and is dependent on the pixel pitch, p, of the detector. For a signal caused by an X-ray beam incident over an entire square pixel centred at x=y=0, its spread to an arbitrary position in the phosphor (x, y) can be calculated by integrating PRF contributions from each area element in the pixel and expressed by the Interpixel Spread Function (ISF), or $$ISF(x, y, E, t_{CsI}) = \int_{-\frac{p}{2}}^{\frac{p}{2}} \int_{-\frac{p}{2}}^{\frac{p}{2}} PRF(x - x', y - y', E, t_{CsI}) dx' dy' \quad (7)$$

Figure 4:
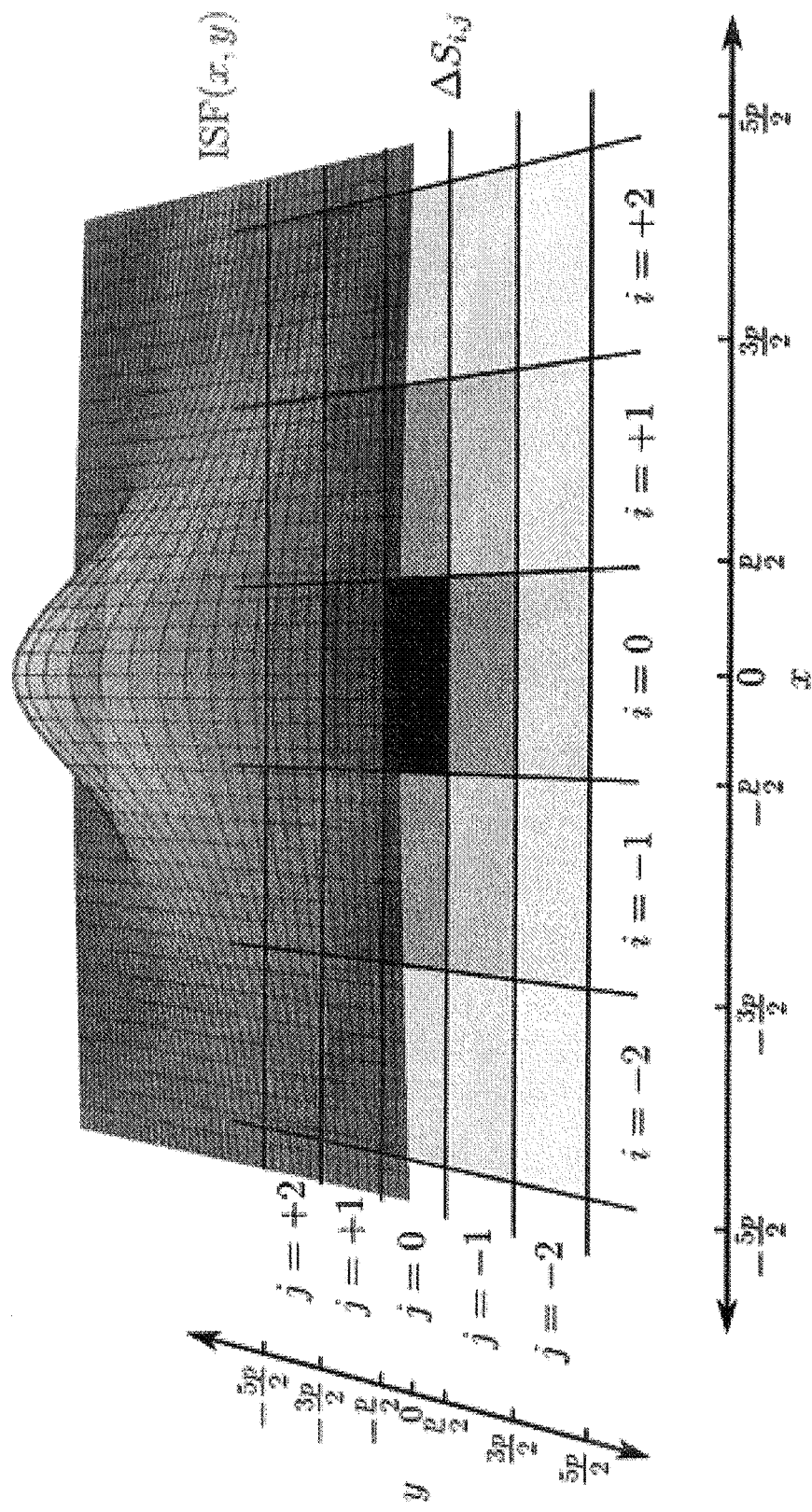
FIG. 4 is an illustration of signal spread in a scintillator.
Figure 5:
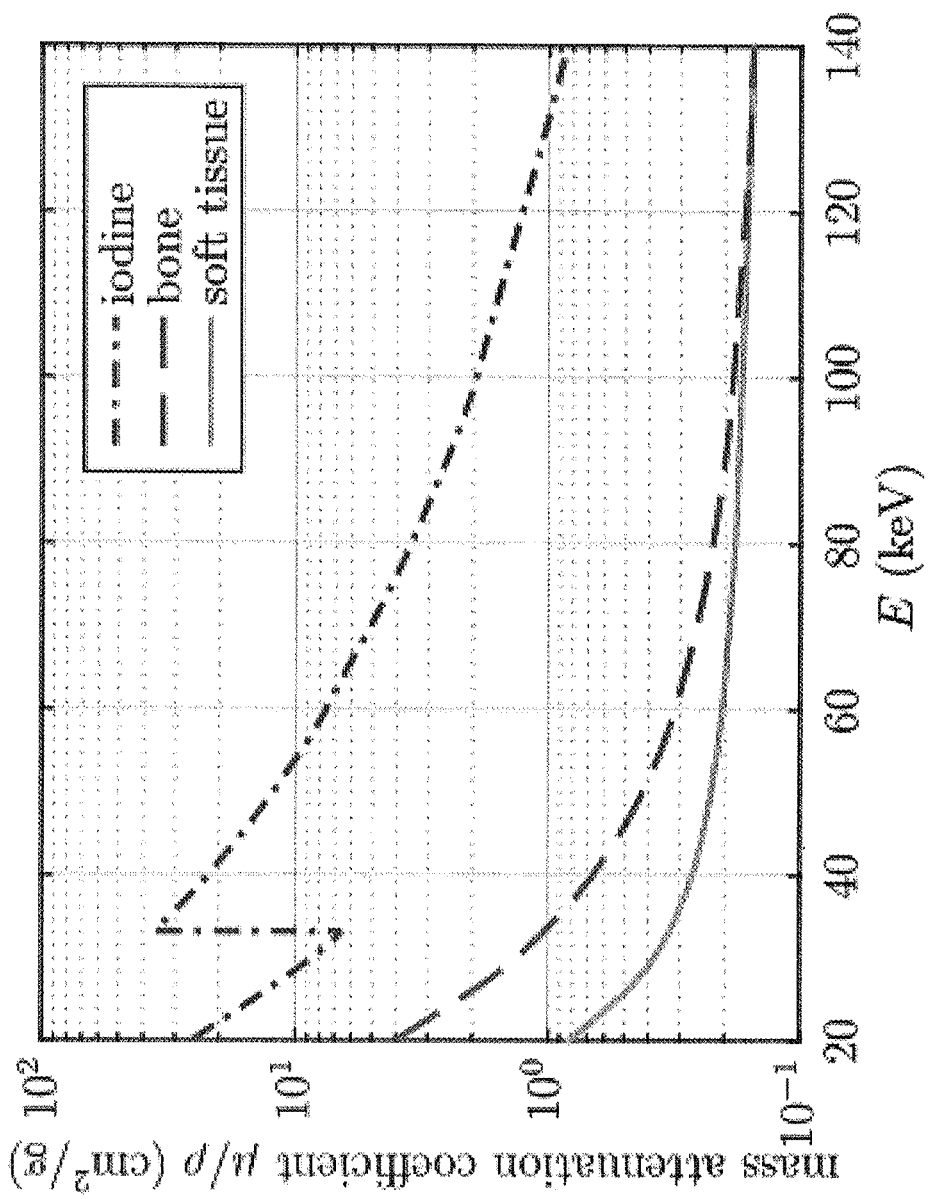
FIG. 5 is a graph of the mass attenuation coefficient for 3 different materials/tissues across the diagnostic X-ray energy range.

The ISF can be used to calculate how the signal incident over a pixel located at i=j=0 will spread to its neighbouring pixels (see FIG. 4). The spread induces an increase signal of $\Delta S_{i,j}$ for the $i^{th}$, $j^{th}$ pixel of the detector array, where this can be calculated using:

$$\Delta S_{i,j}(E, t_{CsI}) = \int_{p(j-\frac{1}{2})}^{p(j+\frac{1}{2})} \int_{p(i-\frac{1}{2})}^{p(i+\frac{1}{2})} ISF(x, y, E, t_{CsI}) dx dy \quad (8)$$

Lastly, a normalized version of $\Delta S(\Delta S')$ can be seen as the smoothing kernel that is applied to an unblurred image as a result of the signal spread. $\Delta S'$ can be fit to a two-dimensional discrete Gaussian kernel of standard deviation $\sigma_G$ since its convolution with a zero-frequency image with normal noise will reduce the image's standard deviation by a factor of $\sim(2\sigma_G\sqrt{\pi})$ for values of $\sigma_G \geq 1/(2\sqrt{\pi})$. The standard deviation of signals generated by a monoenergetic X-ray source can now be updated to include scintillator blur as $$\sigma_s \approx \frac{\sigma'_s}{2\sigma_G^s \sqrt{\pi}} \quad \sigma_h \approx \frac{\sigma'_h}{2\sigma_G^h \sqrt{\pi}} \quad (9)$$

where $\sigma_G^s$ and $\sigma_G^h$ are the standard deviations for the fitted Gaussian kernels of $\Delta S$ for the expected soft tissue and iodinated vessel or calcification signals, respectively.

The above signal spread model is only applicable to the case of a monoenergetic source. However, it can be easily expanded to any source spectrum by first defining an energy-dependent $\sigma_G(E)$, which, at every energy E, would represent the $\sigma_G$ obtained through this process using a pencil beam of that energy. Full polyenergetic signal variances for $\tilde{S}_s$ and $\tilde{S}_h$ can be obtained by including the continuous $\sigma_G^2/4\pi$ as part of the integrand in Equations (5) and (6) (see Equations (17) to (20) for further details).

This model for calculating signal and variance can be extended to the three-layer detector design. In this embodiment example, the detector is improved, or optimized, for operating as a single-shot Dual-Energy detector using the signals of the top and bottom layers. These will be combined to aid in the detection of the aforementioned objects of interest embedded in soft tissue. All other possible modes of image combination using any or all of the three obtained images during an exposure may still operate simultaneously. This is enabled by the unique dual functionality of the intermediate layer. The optimization process does not limit the functionality of this detector in its other modes. However, this example will focus on its mode as a DE imager and will optimize the detector to obtain the best possible enhanced DE images as defined below.

As is the case in any embodiment of this disclosure, the intermediate layer has dual functionality. First, it can generate an image that can be used for other modes or for later enhancement of the generated DE images. Second, it can act as a filter to increase the difference in the mean energy of the incident spectra on the top and bottom layers. This achieves the energy separation needed for obtaining the low-energy and high-energy images required for DE imaging without the need for an extra metal intermediate filter.

The aim of the generated DE images is to remove contrast in the soft tissues (i.e. the tissue type that is not of interest and thereby enhance the objects of interest. This background suppression is attained by exploiting the different rates of change of the tissue's mass attenuation coefficients ($\mu/\rho$) across the diagnostic X-ray energy range. This is shown in the graph of FIG. 4b, where the difference in $\mu/\rho$ between iodine and soft tissue or bone and soft tissue is seen to be higher in the low end of the spectrum (~40 keV) than in the high end (~100 keV). By intelligently combining the images from the top layer (which can be considered the low-energy image) and the image from the bottom layer (which can be considered the high-energy image), the enhanced image with a suppressed background is obtained.

In this example, the logarithmic subtraction method was chosen to combine these two images and obtained the enhanced DE image. Logarithmic subtraction defines an enhanced DE signal (SDE) that aims to suppress soft-tissue using a low-energy signal (in this case, the signal from the top layer St) and a high energy signal (in this case, the signal from the bottom layer Sb) in the following manner:

$$S_{DE}(x,y) = \ln(S_b(x,y)) - w \ln(S_t(x,y)) \quad (10)$$

where w is a weighting factor. This factor is defined such that soft-tissue contrast is canceled as much as possible in the enhanced image and is, preferably, given by the ratio of its attenuation coefficients at high and low energy, $$w = \frac{\mu_s(E_H)}{\mu_s(E_L)} \quad (11)$$

where $E_H$ and $E_L$ are the average energies reaching the bottom and top detector layers when no object is being imaged. These can be calculated using:

$$E_L = \frac{\int_0^\infty \Phi(E) E \, dE}{\int_0^\infty \Phi(E) \, dE} \quad E_H = \frac{\int_0^\infty \Phi(E)(1 - \eta_t(E))(1 - \eta_m(E)) E \, dE}{\int_0^\infty \Phi(E)(1 - \eta_t(E))(1 - \eta_m(E)) \, dE} \quad (12)$$

where $\eta_j = 1 - e^{-\mu C_s J(E) t_j}$ (j=t, i, b are the top, intermediate and bottom layers' quantum efficiencies. Note that due to the broad spectrum of the X-ray source and to the absorption in the object, in practice, the value of w should be slightly tweaked to obtain an improved cancellation, as the ideal 100% cancellation cannot be achieved.

To be able to model the results of logarithmic subtraction, it is necessary to develop an expression for the expected value of the signals at the top and bottom layers at each described X-ray path. The mean value for those pixels within the top layer ($S_t$) for each of the paths of interest (s and h) will follow Equations (1) and (2), as this layer 120a is equivalent to a single-layered detector. The signals for the bottom ($S_b$) layer, however, need to expand on these equations to include the filtration due to the top and intermediate layers. These will therefore become:

$$\overline{S}_{t,s} = A \int_0^\infty \Phi(E) e^{-\mu_s(E)t_s} \eta_t(E) \overline{Q}_{CsI}(E) \, dE \tag{13}$$

$$\overline{S}_{t,h} = A \int_0^\infty \Phi(E) e^{-\mu_s(E)(t_s - t_h) - \mu_h(E)t_h} \eta_t(E) \overline{Q}_{CsI}(E) \, dE \tag{14}$$

$$\overline{S}_{b,s} = A \int_0^\infty \Phi(E) e^{-\mu_s(E)t_s} (1 - \eta_t(E))(1 - \eta_m(E)) \eta_b(E) \overline{Q}_{CsI}(E) \, dE \tag{15}$$

$$\overline{S}_{b,h} = \tag{16}$$
$$A \int_0^\infty \Phi(E) e^{-\mu_s(E)t_s - t_h) - \mu_h(E)t_h} (1 - \eta_t(E))(1 - \eta_m(E)) \eta_b(E) \overline{Q}_{CsI}(E) \, dE$$

The respective variances of these signals will also need to account for the detector design, and can be calculated by expanding Equations (5), (6) and (9) into:

$$\sigma_{t,s}^2 \approx \frac{A}{4\pi} A \int_0^\infty \Phi(E) e^{-\mu_s(E)t_s} \eta_t(E) \overline{Q}_{CsI}^2(E) \sigma_G^{-2}(E, t_t, p) \, dE \tag{17}$$

$$\sigma_{t,h}^2 \approx \frac{A}{4\pi} \int_0^\infty \Phi(E) e^{-\mu_s(E)(t_s - t_h) - \mu_h(E)t_h} \eta_t(E) \overline{Q}_{CsI}^2(E) \sigma_G^{-2}(E, t_t, p) \, dE \tag{18}$$

$$\sigma_{b,s}^2 \approx \frac{A}{4\pi} \int_0^\infty \Phi(E) e^{-\mu_s(E)t_s} (1 - \eta_t(E)) \tag{19}$$
$$(1 - \eta_m(E)) \eta_b(E) \overline{Q}_{CsI}^2(E) \sigma_G^{-2}(E, t_b, p) \, dE$$

$$\sigma_{b,h}^2 \approx \frac{A}{4\pi} \int_0^\infty \Phi(E) e^{-\mu_s(E)(t_s - t_h) - \mu_h(E)t_h} (1 - \eta_t(E)) \tag{20}$$
$$(1 - \eta_m(E)) \eta_b(E) \overline{Q}_{CsI}^2(E) \sigma_G^{-2}(E, t_b, p) \, dE$$

where $\sigma_G(E, t_{C,I}, p)$ represents the standard deviations for a Gaussian kernels fitted to a $\Delta S'$ of a monoenergetic exposure of energy E, a detector of thickness $t_{C,I}$ and a pixel pitch p. The addition of this term and the $\frac{1}{4\pi}$ factor effectively accounts for scintillator blurring.

A method for evaluation image merit using this model is now described. The merit of an enhanced image is defined as depending on the contrast between the two tissue types once soft-tissue has been canceled. In this example, the contrast is defined as the Signal Difference (SD) between two pixels located fully in either one of the paths of interest described above, and can be calculated with:

$$SD = \ln(S_{b,h}) - w\ln(S_{t,h}) - [\ln(S_{b,s}) - w\ln(S_{t,s})] \tag{22}$$
$$= \ln\left(\frac{S_{b,h}}{S_{b,s}}\right) - w\ln\left(\frac{S_{t,h}}{S_{t,s}}\right)$$

The mean value of SD ($\overline{SD}$) can be easily calculated by combining Equations (13) to (16) and (22). In turn, the variance, $\sigma_{SD}^2$, can be taken as a measure of its noise. Assuming no cross-talk between the different layers 120, the noises in the top and bottom layers are uncorrelated, and thus $\sigma_{SD}^2$ can be calculated using:

$$\sigma_{SD}^2 = \left(\frac{1}{\overline{S}_{b,h}^2} \sigma_{b,h}^2 + \frac{1}{\overline{S}_{b,s}^2} \sigma_{b,s}^2\right) + w^2 \left(\frac{1}{\overline{S}_{t,h}^2} \sigma_{t,h}^2 + \frac{1}{\overline{S}_{t,s}^2} \sigma_{t,s}^2\right) \tag{23}$$

It is now possible to define a parameter that can evaluate the detectability of the object of interest in its noisy background. This parameter is chosen to be the Signal Difference to Noise Ratio (SDNR) of the logarithmic subtraction image, and it can be computed as:

$$SDNR = \frac{\overline{SD}}{\sqrt{\sigma_{SD}^2}} \tag{24}$$

SDNR may be considered as the numerical figure of merit for the generated DE image, or FoM. As will be understood, a figure of merit relates to a measurement representing the performance of a device, system or method relative to its alternatives. This number will hence allow for the comparison of the performance as a Dual Energy imager of a specific embodiment of the detector with set manufacturing materials and parameter values.

To determine a preferred configuration of detector parameters in this example, the analytical model developed here was used to calculate FoM for varying values of manufacturing parameters. The parameters investigated in this example where the thicknesses of both the top and the middle scintillator. The bottom scintillator was fixed at 500 μm as a reasonable compromise between increasing quantum efficiency and reducing scintillator blur. A tungsten-anode X-ray source was used for the calculations due to their widespread use is radiography setups. For the sake of calculations, it was assumed to be operating at a peak X-ray tube voltage of 120 kV and to have 3 mm of aluminum filtering.

The two examples applications were investigated. In the first, iodinated vessels of increasing iodine mass loading (Iml) located in 20 cm of soft tissue were considered. In the second, small calcium nodules of varying thickness (tc) in the same soft tissue were evaluated. All mass attenuation and mass energy-absorption coefficients, as well as all material and tissue densities, were obtained from known sources.

The ranges in which both the detector and application parameters were varied during this analysis are detailed below in Table 1.

TABLE 1

Detector parameters and ranges (top 2 rows) and application parameters and ranges (bottom 2 rows) used to improve or optimize the theoretical performance of the detector in this example.

| Symbol | Definition | Range |
|---|---|---|
| $t_t$ | Thickness of top scintillator | 50 μm to 200 μm |
| $t_m$ | Thickness of middle scintillator | 100 μm to 700 μm |
| $I_{ml}$ | Vessel's iodine mass loading | 10 mg/cm² to 75 mg/cm² |
| $t_c$ | Thickness of calcification | 1 mm to 5 mm |

Figure 6A:
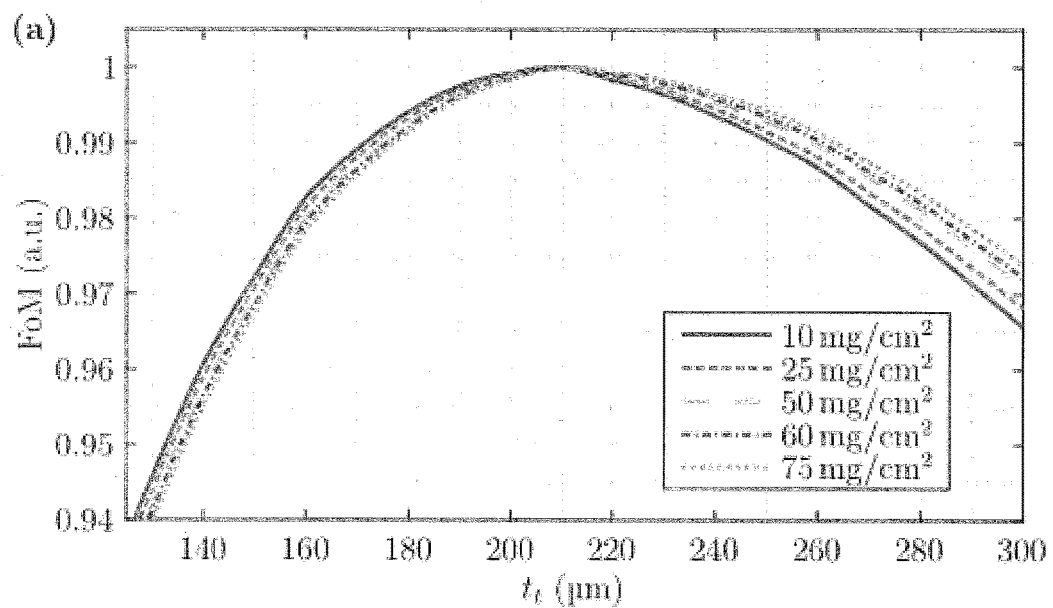
FIG. 6a is a graph showing the figure of merit obtained when varying top scintillator thickness for the iodinated vessel detection application.
Figure 6B:
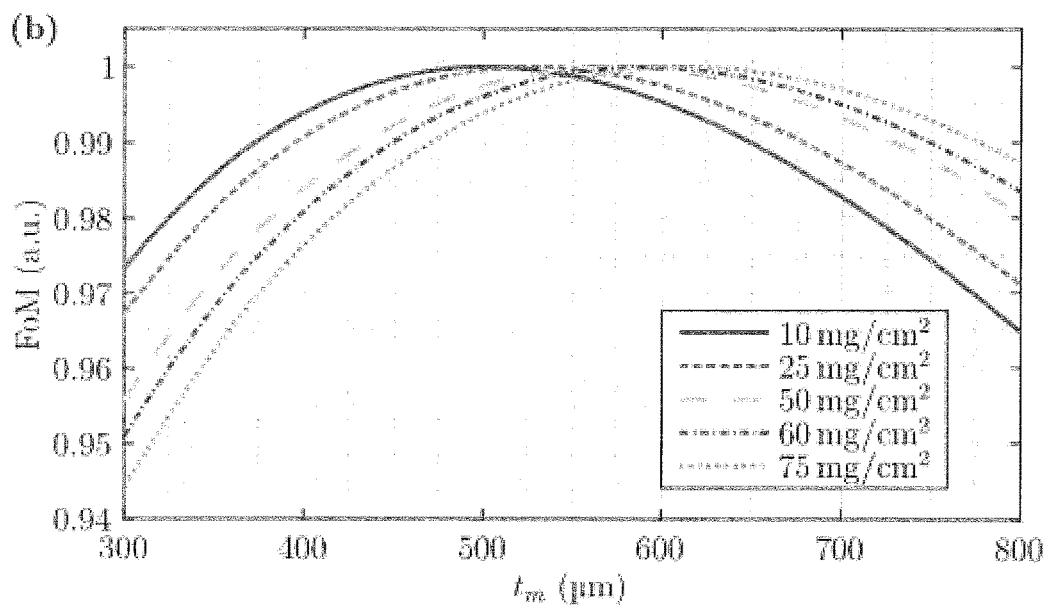
FIG. 6b is a graph showing the figure of merit obtained when varying middle scintillator thickness for the iodinated vessel detection application.
Figure 7A:
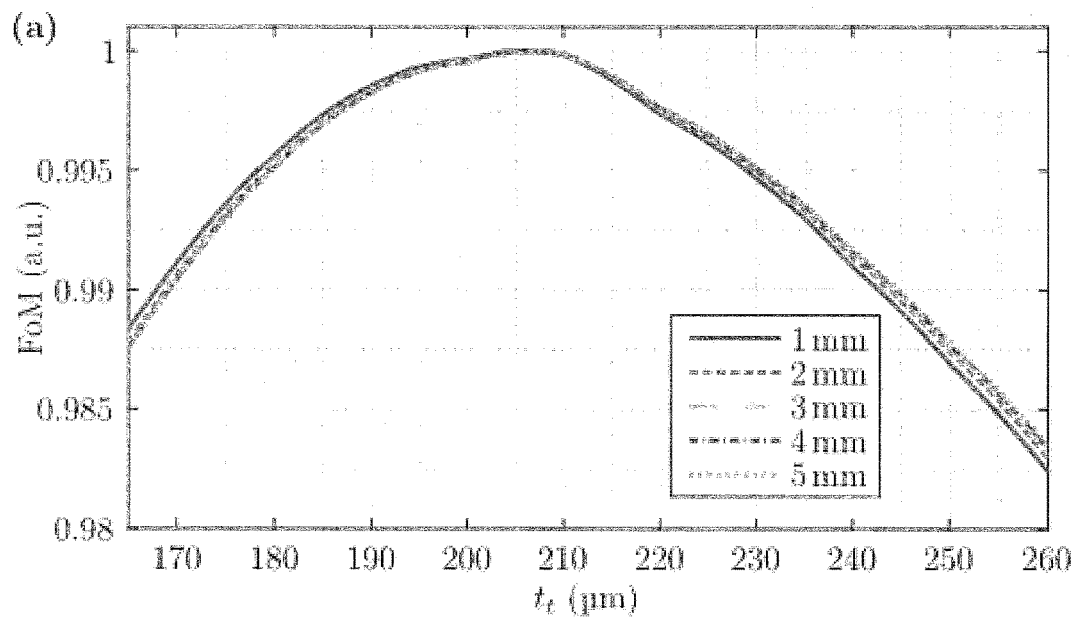
FIG. 7a is a graph showing the figure of merit obtained when varying top scintillator thickness for the calcified nodule detection application.
Figure 7B:
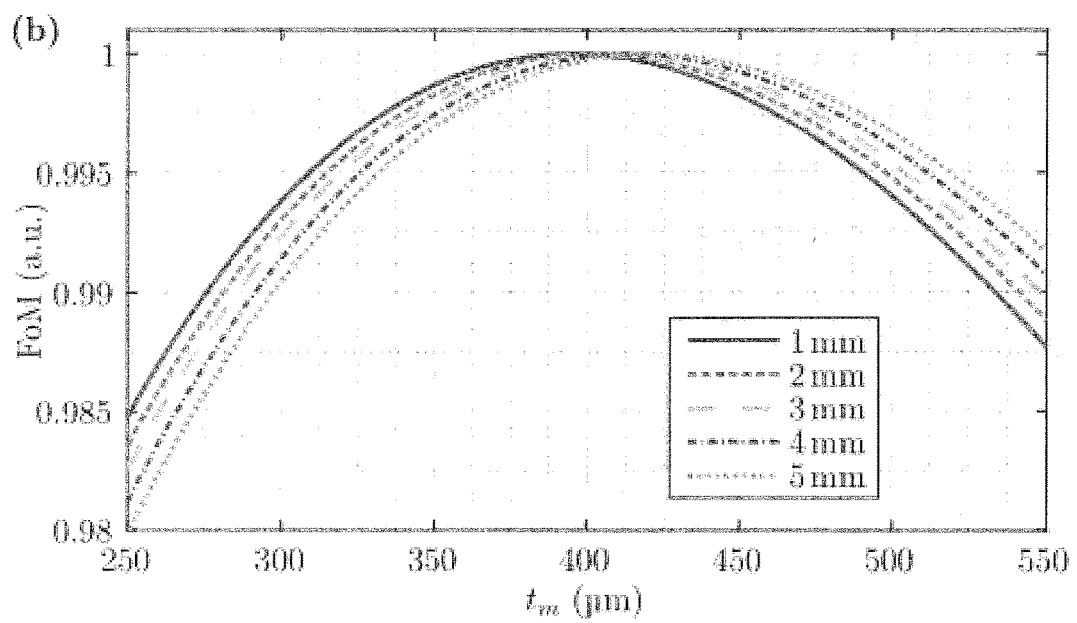
FIG. 7b is a graph showing the figure of merit obtained when varying middle scintillator thickness for the calcified nodule detection application.

The results of this analysis are best illustrated in FIG. 6 and FIG. 7, where it is evident that changing each scintillator thickness will affect the chosen FoM. As such, those detector parameter values that give the best result for a wide range of application parameter values are selected as ideal for these examples. Specifically, in the case of iodinated vessel detection, these values are $t_t$=210 μm and $t_i$=560 μm, while for the case of pulmonary calcifications detection, these are $t_t$=225 μm and $t_m$=440 μm.

With this method, it was therefore possible to choose a particular mode of the presented disclosure (in this example, as a DE detector), and optimize the particular manufacturing parameters for a given application (in this example iodinated vessel and pulmonary calcifications detection). It hence serves as an example of the type of work that developing a specific mode could entail. It is important to reiterate that all other image combination modes will still be able to function in any example of the disclosure, despite what its manufacturing parameters are optimized for.

In the preceding description, for purposes of explanation, numerous details are set forth in order to provide a thorough understanding of the embodiments. However, it will be apparent to one skilled in the art that these specific details may not be required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

The above-described embodiments are intended to be examples only. Alterations, modifications and variations can be effected to the particular embodiments by those of skill in the art without departing from the scope, which is defined solely by the claims appended hereto.

What is claimed is:

1. A method of X-ray imaging comprising:
    obtaining a set of at least three images from a single X-ray exposure, the set of at least three images including a high energy image, an intermediate energy image and a low energy image; and
    manipulating at least two of the at least three images to generate at least one new X-ray image;
    wherein manipulating the at least two of the at least three images includes:
    selecting the high energy image, the intermediate energy image and the low energy image;
    combining the high energy image and the intermediate energy image to generate an intermediate-high enemy image;
    combining the low energy image and the intermediate energy image to generate an intermediate-low energy image; and
    performing a weighted subtraction of at least two of the high energy image, the intermediate-high energy image, the intermediate energy image, the intermediate-low energy image and the low energy image to generate an enhanced dual energy image.

2. The method of claim 1 further comprising:
    displaying the at least one enhanced X-ray image.

3. The method of claim 1 further comprising:
    combining the at least three images to generate a full spectrum X-ray image.

4. A method of X-ray imaging comprising:
    obtaining a set of at least three images from a single X-ray exposure, the set of at least three images including a high energy image, an intermediate energy image and a low energy image;
    selecting the high energy image, the intermediate energy image and the low energy image;
    extracting intermediate energy image data for use with statistical algorithms to enhance the signal-to-noise ratio of the low energy image and the high energy image; and
    performing a weighted subtraction of the enhanced high energy image and the enhanced low energy image to generate a higher signal-to-noise ratio dual energy image.

5. The method of claim 4 further comprising:
    displaying the at least one enhanced X-ray image.

6. The method of claim 4 further comprising:
    combining the at least three images to generate a full spectrum X-ray image.

\* \* \* \* \*